United States Patent [19]

Matsuura

[11] Patent Number: 5,138,100

[45] Date of Patent: Aug. 11, 1992

[54] METHOD FOR PREPARING METHACROLEIN

[75] Inventor: Ikuya Matsuura, Toyama, Japan

[73] Assignee: Mitsui Toatsu Chemicals, Inc., Tokyo, Japan

[21] Appl. No.: 711,198

[22] Filed: Jun. 6, 1991

[30] Foreign Application Priority Data

Jun. 6, 1990 [JP] Japan .................. 2-146297

[51] Int. Cl.$^5$ ............... C07C 45/37; C07C 45/33
[52] U.S. Cl. .................. 568/474; 568/472; 568/476; 568/479
[58] Field of Search .............. 568/469.9, 470, 471, 568/474, 475, 476, 477, 479, 480, 481, 472

[56] References Cited

U.S. PATENT DOCUMENTS

| | | | |
|---|---|---|---|
| 3,497,461 | 2/1970 | McClellan et al. | 252/437 |
| 3,972,920 | 8/1976 | Ishii et al. | 568/477 |
| 4,012,449 | 3/1977 | Shikakura et al. | 568/477 |
| 4,035,418 | 7/1977 | Okada et al. | 568/477 |
| 4,111,984 | 7/1978 | Ishii et al. | 568/477 |
| 4,111,985 | 9/1978 | Okada et al. | 568/477 |
| 4,219,670 | 8/1980 | Okada et al. | 568/477 |
| 4,306,090 | 12/1981 | Kirch et al. | 568/481 |
| 4,388,223 | 6/1983 | Ferlazzo et al. | 252/437 |
| 4,479,013 | 10/1984 | Khoobiar | 568/479 |
| 4,816,603 | 3/1989 | Oh-Kita et al. | 568/477 |
| 4,968,846 | 11/1990 | Kuragano et al. | 568/476 |

FOREIGN PATENT DOCUMENTS 0061830 10/1982 European Pat. Off. .
1555679 10/1968 France .

Primary Examiner—Werren B. Lone
Attorney, Agent, or Firm—Oblon, Spivak, McClelland, Maier & Neustadt

[57] ABSTRACT

A method for preparing methacrolein comprises subjecting isobutylene or a tertiary butanol to gas phase catalytic oxidation with molecular oxygen in the presence of a catalyst which comprises a mixture of a composition (I) represented by the following general formula I:

$$Mo_a Bi_b Fe_c X_d Y_e Z_f O_g \qquad I$$

wherein X represents at least one element selected from the group consisting of Ni and Co; Y represents at least one element selected from the group consisting of K, Rb, Cs and Tl; Z represents at least one element selected from the group consisting of those belonging to Group 2, 3, 4, 5, 6, 7, 11, 12, 13, 14, 15 and 16 of Periodic Table in accordance with IUPAC nomenclature (1989); and a, b, c, d, e, f and g each represents an atomic ratio of each corresponding element, when a is assumed to be 12, b is 0.1 to 10, c is 0 to 20, d is 0 to 20, e is 0 to 2, f is 0 to 4 and g is the number of oxygen atoms which is required for satisfying the valencies of the foregoing elements and a composition (II) represented by the following general formula II:

$$Ln_h Mo_i O_j \qquad II$$

wherein Ln represents at least one element selected from the group consisting of rare earth elements; h, i and j each represents an atomic ratio of each corresponding element, when i is assumed to be 1, h is 0.2 to 1.5 and j is the number of oxygen atoms which is required for satisfying the valencies of the foregoing elements. According to this method, the end product is obtained with a high yield and selectivity.

3 Claims, No Drawings

METHOD FOR PREPARING METHACROLEIN

BACKGROUND OF THE INVENTION

1. Field of the Invention

The present invention relates to a method for preparing methacrolein through gas phase catalytic oxidation of isobutylene or a tertiary butanol with molecular oxygen.

2. Description of the Prior Art

Heretofore, there have been proposed a variety of catalysts used in the preparation of methacrolein through gas phase catalytic oxidation of isobutylene or a tertiary butanol with molecular oxygen For instance, Japanese Unexamined Patent Publication No. Sho 63-107745 discloses a catalyst which comprises a rare earth element. The patent also discloses that antimony is an essential component in order to obtain a catalyst having high selectivity to end products and that it is necessary to use, as a starting material for the catalyst, antimony trioxide having an average particle size of the order of 0.2 μm or smaller which cannot be obtained through methods other than the metal vapor deposition method. Moreover, Japanese Unexamined Patent Publication No Sho 63-315147 also discloses a catalyst which comprises a rare earth element, but the catalyst is prepared according to a special method and the activity and selectivity thereof are not yet sufficient.

As has been discussed above, the conventional catalysts for preparing methacrolein are still insufficient in the quality thereof such as the activity, the selectivity to methacrolein, the stability and the duration of life thereof. Thus, there have been desired for the improvement of the quality of these catalysts.

SUMMARY OF THE INVENTION

Accordingly, an object of the present invention is to provide a catalyst which has high activity and stability and is excellent in the selectivity to methacrolein.

Another object of the present invention is to provide a method for preparing methacrolein in high yield and selectivity through gas phase catalytic oxidation of isobutylene or a tertiary butanol with molecular oxygen.

The inventors have diligently studied the components, composition and method for preparation of catalysts used in the preparation of methacrolein through gas phase catalytic oxidation of isobutylene or a tertiary butanol with molecular oxygen, in particular those comprising Mo and Bi as essential components and preferably at least one member selected from the group consisting of Fe, Ni and Co in order to develop a catalyst having high activity and excellent selectivity to methacrolein and as a result, have found out that a catalyst obtained by mechanically mixing the composition comprising the foregoing components and a compound oxide containing Ce and Mo and then calcining the resulting mixture exhibits quite excellent activity and selectivity to methacrolein.

According to the present invention, there is thus provided a method for preparing methacrolein which comprises subjecting isobutylene or a tertiary butanol to gas phase catalytic oxidation with molecular oxygen in the presence of a catalyst which comprises a mixture of a composition (I) represented by the following general formula I:

$$Mo_a Bi_b Fe_c X_d Y_e Z_f O_g \qquad \text{I}$$

wherein X represents at least one element selected from the group consisting of Ni and Co; Y represents at least one element selected from the group consisting of K, Rb, Cs and Tl; Z represents at least one element selected from the group consisting of those belonging to Groups 2, 3, 4, 5, 6, 7, 11, 12, 13, 14, 15 and 16 of Periodic Table in accordance with IUPAC nomenclature (1989) and specifically, represents at least one element selected from the group consisting of Be, Mg, Ca, Sr, Ba, Ti, Zr, Ce, Nb, Cr, W, Mn, Cu, Ag, Zn, Cd, B, Al, Ge, Sn, Pb, P, As, Sb, S, Se and Te; a, b, c, d, e, f and g each represents the atomic ratio of each corresponding element, when a is assumed to be 12, b is 0.1 to 10, c is 0 to 20, d is 0 to 20, e is 0 to 2, f is 0 to 4 and g is the number of oxygen atoms which is required for satisfying the valencies of the foregoing elements and a composition (II) represented by the following general formula II:

$$Ln_h Mo_i O_j \qquad \text{II}$$

wherein Ln represents at least one element selected from the group consisting of rare earth elements; h, i and j each represents the atomic ratio of each corresponding element, when i is assumed to be 1, h is 0.2 to 1.5 and j is the number of oxygen atoms which is required for satisfying the valencies of the foregoing elements.

DETAILED DESCRIPTION OF THE INVENTION

In the method of the present invention, a catalyst composed of the composition (I) only has low activity, requires a high reaction temperature and exhibits a low selectivity to methacrolein as compared with the catalyst which comprises compositions (I) and (II) as will be confirmed in Comparative Examples 1 and 2 hereinafter given. On the other hand, a catalyst composed of the composition (II) only has a low activity and exhibits no selectivity to methacrolein at all as will be confirmed in Comparative Example 3 given below.

The catalyst of the present invention obtained by mixing these compositions (I) and (II) exhibits a high activity and thus, the desired reaction proceeds at a temperature lower than that required for the conventional catalysts. For this reason, the end products such as methacrolein hardly undergo any oxidation which is liable to be observed at a high temperature and, therefore, the catalyst is excellent in the selectivity to methacrolein.

In composition (II), the atomic ratio of the rare earth element (Ln) to molybdenum (Mo) ranges from 0.2 to 1.5 and preferably 0.5 to 1.0. This is because, if the atomic ratio, Ln/Mo, is less than 0.2, the selectivity to methacrolein is improved, but the activity thereof is not improved, while if the atomic ratio, Ln/Mo, exceeds 1.5, the activity is enhanced, but the selectivity is impaired. Moreover, composition (I) and composition (II) are mixed so that the weight ratio of composition (II) to composition (I) ranges from 0.001 to 0.2 and preferably 0.01 to 0.1. This is because, if the weight ratio, composition (II)/composition (I), is less than 0.001, the selectivity to methacrolein is improved, but the activity thereof is not improved, while if the weight ratio exceeds 0.2, the activity is improved, but the selectivity is impaired.

Compositions (I) and (II) used in the method of the present invention can be prepared according to any method known in the art, for instance, the following method:

Composition (I) can be prepared by dissolving a proper molybdate such as ammonium molybdate in pure water with heating, optionally adding a salt of at least one element selected from the group consisting of K, Rb, Cs and Tl to the resulting solution, adding a compound of Bi in the form of an aqueous solution, optionally adding a compound of Fe, Co and/or Ni in the form of an aqueous solution, optionally adding a compound of at least one element selected from the group consisting of Be, Mg, S, Ca, Sr, Ba, Te, Se, Ce, Ge, Mn, Zn, Cr, Ag, Sb, Pb, As, B, P, Nb, Cu, W, Cd, Sn, Al, Zr and Ti, optionally adding a carrier such as $SiO_2$, drying the resulting muddy suspension, calcining and then burning at a temperature ranging from 400° to 650° C.

In addition, composition (II) can be prepared according to either of the following methods:

(1) A proper molybdate such as ammonium molybdate is dissolved in pure water under heating, an aqueous solution of the nitrate of a desired rare earth element is added to the solution, the mixture is neutralized with aqueous ammonia, subjected to a heat treatment, the resulting precipitates are washed with water and then calcined at a temperature of 500° C. or lower.

(2) An aqueous solution of the nitrate of a desired rare earth element is neutralized with aqueous ammonia, the resulting precipitates and molybdic acid are mixed with heating while optionally adding distilled water and the resulting mixture is calcined at a temperature of not more than 500° C.

The composition (II) thus prepared shows a strong diffraction line near the position corresponding to d ranging from 3.13 to 3.17 Å as determined by an XRD measurement. In addition, if Ce, Pr and/or Tb are used as the rare earth elements, composition (II) shows a diffraction line near the position corresponding to d ranging from 3.4 to 3.8Å depending on the conditions for the preparation.

The catalyst used in the method of the present invention can be prepared by mixing compositions (I) and (II) in a weight ratio, composition (I)/composition (II), ranging from 0.001 to 0.2, preferably 0.01 to 0.1, optionally adding water, mixing these ingredients under heating, evaporating the mixture to dryness and then calcining it at a temperature ranging from 400° to 650° C.

Materials for preparing the catalyst used in the method of the present invention are preferably compounds which can be decomposed into the desired oxides during the processes for preparing the catalyst. Examples of such compounds are nitrates such as cobalt nitrate, ferric nitrate, bismuth nitrate and cerium nitrate, ammonium salts, organic acid salts, hydroxides such as potassium hydroxide and cerium hydroxide, oxides such as molybdenum trioxide, metallic acid and ammonium salts of metallic acids such as ammonium molybdate.

As materials for silica, there may be used, for instance, silica sol, silica gel, silicic acid esters and silicates.

The catalyst in the present invention may have a variety of shapes such as a particulate form and a molded body and can be used in the form of a fixed bed as well as a moving bed or a fluidized bed.

The catalytic gas phase oxidation in the method of the present invention can be carried out by passing, through a layer of the foregoing catalyst, a mixed gas, as a starting gas, which comprises 1 to 10% by volume of isobutylene or a tertiary butanol, 3 to 20% by volume of molecular oxygen and 70 to 96% by volume of a diluent gas at a temperature ranging from 250° to 450° C. and a pressure of from ordinary pressure to 10 atm and at a space velocity of from 300 to 5,000/hr.

As molecular oxygen, air is in general used, but pure oxygen may likewise be employed.

As the diluent gases, inert gases such as nitrogen gas and carbon dioxide gas can, for instance, be used. It is also possible to circulate a part of the incompressible gas included in the reaction gas mixture as the diluent gas.

It is preferred to simultaneously use water vapor, as the diluent gas, from the viewpoint of the improvement of the activity and selectivity of the resulting catalyst. In such case, water vapor is in general added to the starting gas mixture in an amount of up to 60% by volume.

The present invention will hereinafter be explained in more detail with reference to the following non-limitative working Examples and Comparative Examples.

In the following Examples and Comparative Examples, the conversion rate, the selectivity and the yield are defined as follows:

$$\text{Conversion Rate (\%)} = \frac{\text{molar number of reacted i-}C_4' \text{ or TBA}}{\text{molar number of i-}C_4' \text{ or TBA supplied}} \times 100$$

$$\text{Rate of Selectivity (\%)} = \frac{\text{molar number of MAL formed}}{\text{molar number of reacted i-}C_4' \text{ or TBA}} \times 100$$

$$\text{Yield (\%)} = \frac{\text{molar number of MAL formed}}{\text{molar number of i-}C_4' \text{ or TBA supplied}} \times 100$$

In the foregoing definition, i-$C_4'$ means isobutylene, TBA means tertiary butanol and MAL means methacrolein.

EXAMPLE 1

A solution A was prepared by adding 127.2 g of ammonium molybdate to 1,200 ml of water while heating and stirring the water to thus dissolve the salt in water. Separately, a solution B was prepared by dissolving 139.6 g of cobalt nitrate and 72.20 g of ferric nitrate in 180 ml of water. Further, a solution C was prepared by dissolving 28.57 g of bismuth nitrate in an aqueous nitric acid solution which comprised 15 ml of a 60% nitric acid solution and 150 ml of water. To solution A, there were in order dropwise added solutions B and C, the resulting slurry was subjected to spray-drying and then calcination at 300° C. to give a composition (I) having an atomic ratio, Mo/Bi/Fe/Co, of 12/1/3/8.

A solution D was prepared by adding 31.8 g of ammonium molybdate to 300 ml of water while heating and stirring the water to thus dissolve the salt in water. A solution E was separately prepared by dissolving 35.2 g of cerium nitrate in an aqueous nitric acid solution which comprised 10 ml of a 60% nitric acid solution and 100 ml of water. Solution E was dropwise added to and mixed with solution D, then the mixture was neutralized with aqueous ammonia, heated at 100° C. for 8 hours with stirring, the resulting precipitates were sufficiently washed with water, dried and calcined at 300° C. to give a composition (II) having an atomic ratio, Ce/Mo, of 0.5/1.

Compositions (I) and (II) were mixed together so that the weight ratio (composition (II)/composition (I)) was equal to 0.01, followed by the addition of distilled water, stirring and mixing for 16 hours under heating, drying at 120° C. for 12 hours and then calcination at 540° C. for 4 hours to give a catalyst.

The resulting catalyst (1 ml) was charged in a usual tubular reactor, a starting gas mixture comprising 8.3% by volume of isobutylene, 16.7% by volume of oxygen, 8.3% by volume of water vapor and the balance (66.7% by volume) of nitrogen was passed through the layer of the catalyst at a temperature of 300° C. and at a space velocity of 3600/hr to perform the reaction and to thus evaluate the quality of the catalyst. The results thus obtained are listed in the following Table 1.

EXAMPLES 14 TO 16 AND COMPARATIVE EXAMPLE 4 AND 5

According to the same manner used in Example 1, catalysts were prepared by mixing a composition (I) prepared in the same manner used in Example 1 except that the atomic ratio, Mo//Bi/Fe/Co, was equal to 2/3/0/0 and each composition (II) having a corresponding atomic ratio as listed in Table 2 and prepared in the same manner used in Example 1 so that each weight ratio, composition (II)/composition (I), was equal to that given in Table 2.

The performances of each resulting catalyst were evaluated in the same manner used in Example 1. The results thus obtained are summarized in Table 2.

TABLE 1

| Ex. No. | Oxide Components of Comp. (II) | | Wt. Ratio (II)/(I) | Reaction Temp. (°C.) | Performances of Catalyst | | |
|---|---|---|---|---|---|---|---|
| | Kind of Ln | Atomic Ratio Ln/Mo | | | Conv. (%) | Sel. (%) | Yield (%) |
| 1 | Ce | 0.5 | 0.01/1.00 | 300 | 89.5 | 94.5 | 93.1 |
| 2 | Ce | 0.5 | 0.05/1.00 | 300 | 98.7 | 97.1 | 95.8 |
| 3 | Ce | 0.5 | 0.10/1.00 | 300 | 96.3 | 94.0 | 90.5 |
| 4 | Ce | 1.0 | 0.01/1.00 | 300 | 84.9 | 92.7 | 78.8 |
| 5 | Ce | 1.0 | 0.05/1.00 | 300 | 96.4 | 93.6 | 90.2 |
| 6 | Ce | 1.0 | 0.10/1.00 | 300 | 98.9 | 92.7 | 91.7 |
| 7 | Pr | 0.5 | 0.05/1.00 | 340 | 99.0 | 94.0 | 93.1 |
| 8 | Nd | 0.5 | 0.05/1.00 | 360 | 95.3 | 93.5 | 89.1 |
| 9 | Pm | 0.5 | 0.05/1.00 | 360 | 92.7 | 93.0 | 86.0 |
| 10 | Sm | 0.5 | 0.05/1.00 | 360 | 97.3 | 92.0 | 89.5 |
| 11 | Eu | 0.5 | 0.05/1.00 | 360 | 99.1 | 93.0 | 92.2 |
| 12 | Gd | 0.5 | 0.05/1.00 | 360 | 95.1 | 91.3 | 86.8 |
| 13 | Tb | 0.5 | 0.05/1.00 | 340 | 98.3 | 94.5 | 92.9 |
| 1* | — | — | 0.00/1.00 | 400 | 90.3 | 82.3 | 74.3 |
| 2* | — | — | 0.00/1.00 | 340 | 14.3 | 85.4 | 12.2 |
| 3* | Ce | 0.5 | 1.00/1.00 | 340 | 18.3 | 6.4 | 1.7 |

TABLE 2

| Ex. No. | Oxide Components of Comp. (II) | | Wt. Ratio (II)/(I) | Reaction Temp. (°C.) | Performances of Catalyst | | |
|---|---|---|---|---|---|---|---|
| | Kind of Ln | Atomic Ratio Ln/Mo | | | Conv. (%) | Sel. (%) | Yield (%) |
| 14[1) | Ce | 0.5 | 0.10/1.00 | 340 | 89.6 | 90.6 | 81.2 |
| 15[1) | Ce | 0.5 | 0.20/1.00 | 340 | 90.3 | 87.3 | 78.8 |
| 16 | Pr | 0.5 | 0.10/1.00 | 340 | 82.7 | 88.9 | 73.5 |
| 4* | — | — | 0.00/1.00 | 400 | 41.0 | 83.8 | 34.4 |
| 5* | — | — | 0.00/1.00 | 340 | 0.0 | — | — |
| 3*[1) | Ce | 0.5 | 1.00/0.00 | 340 | 18.3 | 6.4 | 1.7 |

*: Comparative Example
[1): There were observed strong diffraction lines at the position corresponding to d = 3.4 to 3.8 Å. in the XRD spectra of Examples 14 and 15 and Comparative Example 3.
Conv.: conversion; Sel.: selectivity

EXAMPLE 2 TO 13 AND COMPARATIVE EXAMPLE 1 TO 3

According to the same manner used in Example 1, catalysts were prepared by mixing a composition (I) which had been prepared in the same manner used in Example 1 with each composition (II) which had the corresponding atomic ratio as listed in Table 1 and had been prepared in the same manner used in Example 1 so that each weight ratio, composition (II) /composition (I), was equal to that listed in Table 1.

The performances of each resulting Catalyst were evaluated in the same manner used in Example 1. The results obtained are summarized in Table 1.

COMPARATIVE EXAMPLES 6 TO 8

In order to make clear the effect attained by the catalyst of the present invention which is obtained by mixing the compositions (I) and (II), a catalyst having the same composition as that for the mixed catalyst was prepared by a batchwise method in accordance with the same manner as used in Example 1 for preparing the composition (I). The performances of the resulting catalyst were evaluated in the same manner used in Example 1. The results obtained are summarized in the following Table 3.

TABLE 3

| Ex. No. | Composition of Catalyst | | | | | | Reaction Temp. (°C.) | Performances of Catalyst | | |
|---|---|---|---|---|---|---|---|---|---|---|
| | Mo | Bi | Fe | Co | Ln | Note | | Conv. (%) | Sel. (%) | Yield (%) |
| 6* | 12.6 | 1 | 3 | 8 | Ce 0.3 | the same as Ex. 2 | 340 | 97.9 | 80.5 | 78.8 |
| 7* | 13.3 | 1 | 3 | 8 | Ce 0.6 | the same as Ex. 3 | 340 | 98.0 | 78.9 | 77.3 |

TABLE 3-continued

| Ex. No. | Composition of Catalyst | | | | | | Reaction Temp. (°C.) | Performances of Catalyst | | |
|---|---|---|---|---|---|---|---|---|---|---|
| | Mo | Bi | Fe | Co | Ln | Note | | Conv. (%) | Sel. (%) | Yield (%) |
| 8 *[1) | 4.9 | 6 | 0 | 0 | Ce 0.4 | the same as Ex. 14 | 400 | 78.8 | 57.4 | 45.2 |

\* : Comparative Example
[1): The catalyst of Comparative Example 8 did not show any XRD spectrum near the position corresponding to d = 3.4 to 3.8 Å unlike the catalyst of Example 14

I claim:

1. A method for preparing methacrolein comprising subjecting isobutylene or a tertiary butanol to gas phase catalytic oxidation with molecular oxygen in the presence of a catalyst which comprises a mixture of a composition (I) represented by the following general formula I:

$$Mo_a Bi_b Fe_c X_d Y_e Z_f O_g \qquad I$$

wherein X represents at least one element selected from the group consisting of Ni and Co; Y represents at least one element selected from the group consisting of K, Rb, Cs and Tl; Z represents at least one element selected from the group consisting of Be, Mg, Ca, Sr, Ba, Ti, Zr, Ce, Nb, Cr, W, Mn, Cu, Ag, Zn, Cd, B, Al, Ge, Sn, Pb, P, As, Sb, S, Se and Te; and a, b, c, d, e, f and g each represents an atomic ratio of each corresponding element, when a is 12, b is 0.1 to 10, c is 0 to 20, d is 0 to 20, e is 0 to 2, f is 0 to 4 and g is the number of oxygen atoms which is required for satisfying the valencies of the foregoing elements and a composition (II) represented by the following general formula II:

$$Ln_h Mo_i O_j \qquad II$$

wherein Ln represents at least one element selected from the group consisting of rare earth elements; h, i and j each represents an atomic ratio of each corresponding element, when i is 1, h is 0.2 to 1.5 and j is the number of oxygen atoms which is required for satisfying the valencies of the foregoing elements.

2. The method as set forth in claim 1 wherein the weight ratio of composition (I) to composition (II) ranges from 1: 0.001 to 1:0.2.

3. The method as set forth in claim 1 wherein the composition (II) comprises a composite oxide which exhibits a strong diffraction line near a position corresponding to d ranging from 3.4 to 3.8Å as determined by an XRD measurement.